(12) United States Patent
Durkin et al.

(10) Patent No.: US 6,743,222 B2
(45) Date of Patent: Jun. 1, 2004

(54) METHOD OF TREATING DISORDERS ASSOCIATED WITH SEBACEOUS FOLLICLES

(75) Inventors: Anthony J. Durkin, Costa Mesa, CA (US); Dilip Y. Paithankar, Natick, MA (US)

(73) Assignee: Candela Corporation, Wayland, MA (US)

( * ) Notice: Subject to any disclaimer, the term of this patent is extended or adjusted under 35 U.S.C. 154(b) by 0 days.

(21) Appl. No.: 09/731,496

(22) Filed: Dec. 7, 2000

(65) Prior Publication Data

US 2001/0041886 A1 Nov. 15, 2001

Related U.S. Application Data (60) Provisional application No. 60/170,244, filed on Dec. 10, 1999.

(51) Int. Cl.[7] .................................................. A61B 18/18
(52) U.S. Cl. .................... 606/9; 606/10; 606/13; 606/22; 606/27; 606/3; 607/88; 607/89
(58) Field of Search ............................... 606/9, 2, 3, 10, 606/11, 13, 20, 22, 23, 27, 32, 33; 128/898; 607/88, 89, 96, 100, 101, 108, 109, 110

(56) References Cited

U.S. PATENT DOCUMENTS

| | | | |
|---|---|---|---|
| 4,874,361 A | 10/1989 | Obagi | |
| 5,226,907 A | 7/1993 | Tankovich | |
| 5,304,170 A | 4/1994 | Green | |
| 5,423,803 A | 6/1995 | Tankovich et al. | |
| 5,425,728 A | 6/1995 | Tankovich | |
| 5,464,436 A | * 11/1995 | Smith | 607/89 |
| 5,549,660 A | 8/1996 | Mendes et al. | |
| 5,569,663 A | 10/1996 | Ribier et al. | |
| 5,643,334 A | 7/1997 | Eckhouse et al. | 607/788 |
| 5,679,691 A | 10/1997 | Ribier et al. | |
| 5,713,845 A | 2/1998 | Tankovich | |

(List continued on next page.)

FOREIGN PATENT DOCUMENTS

| | | |
|---|---|---|
| AU | B-60343/90 | 6/1992 |
| DE | 198 32 221 C2 | 7/2000 |
| EP | 1 147 785 A2 | 10/2001 |
| WO | WO 91/01727 | 2/1991 |
| WO | 97/37723 | 10/1997 |
| WO | 99/07438 | 2/1999 |
| WO | 99/49937 | 10/1999 |
| WO | 00/02491 | 1/2000 |
| WO | 00/09023 | 2/2000 |
| WO | 00/32272 | 6/2000 |
| WO | 00/64537 | 11/2000 |

OTHER PUBLICATIONS

Anderson et al., (1981) "The Optics of Human Skin" *The Journal of Investigative Dermatology*, 77(1):13–19.

(List continued on next page.)

*Primary Examiner*—Henry Bennett
*Assistant Examiner*—Fadi H. Dahbour
(74) *Attorney, Agent, or Firm*—Testa, Hurwitz & Thibeault (57) ABSTRACT

Disclosed herein is a method of treating mammalian, for example, human, skin afflicted with a sebaceous follicle disorder, for example, acne. The method involves cooling an exposed surface of a region afflicted with the disorder and applying energy, for example, energy from a coherent or incoherent light source, to the region. The applied energy reduces the size and/or density of lesions associated with the disorder in the treated region, and can reduce or otherwise alleviate lesion-associated skin inflammation in the treated region. Cooling preserves the surface, for example, epidermis, of the skin. The method, therefore, is effective at treating the disorder while at the same time avoiding or minimizing thermal damage to the exposed surface of the skin.

30 Claims, 5 Drawing Sheets

U.S. PATENT DOCUMENTS

| | | | |
|---|---|---|---|
| 5,735,844 | A | 4/1998 | Anderson et al. |
| 5,746,736 | A | 5/1998 | Tankovich |
| 5,752,948 | A | 5/1998 | Tankovich et al. |
| 5,752,949 | A | 5/1998 | Tankovich et al. |
| 5,760,407 | A | 6/1998 | Margosiak et al. |
| 5,800,479 | A | 9/1998 | Thiberg |
| 5,810,801 | A * | 9/1998 | Anderson et al. ............... 606/9 |
| 5,814,040 | A | 9/1998 | Nelson et al. |
| 5,817,089 | A | 10/1998 | Tankovich et al. |
| 5,817,090 | A * | 10/1998 | Abergel et al. ................ 606/9 |
| 5,820,626 | A | 10/1998 | Baumgardner |
| 5,836,999 | A | 11/1998 | Eckhouse et al. |
| 5,871,480 | A | 2/1999 | Tankovich |
| 5,880,292 | A | 3/1999 | DeLuca et al. |
| 5,897,549 | A | 4/1999 | Tankovich |
| 5,925,035 | A | 7/1999 | Tankovich |
| 5,984,915 | A * | 11/1999 | Loeb et al. .................... 606/9 |
| 6,030,378 | A | 2/2000 | Stewart |
| 6,036,684 | A | 3/2000 | Tankovich et al. |
| 6,050,990 | A | 4/2000 | Tankovich et al. |
| 6,059,820 | A | 5/2000 | Baronov |
| 6,063,074 | A | 5/2000 | Tankovich |
| 6,063,108 | A * | 5/2000 | Salansky et al. ............... 607/89 |
| 6,083,217 | A | 7/2000 | Tankovich |
| 6,135,994 | A * | 10/2000 | Chernoff ........................ 606/9 |
| 6,152,917 | A | 11/2000 | Tankovich |
| 6,162,211 | A | 12/2000 | Tankovich et al. |
| 6,168,590 | B1 * | 1/2001 | Neev .............................. 606/9 |
| 6,176,854 | B1 * | 1/2001 | Cone ........................... 606/10 |
| 6,235,016 | B1 | 5/2001 | Stewart |
| 6,267,771 | B1 | 7/2001 | Tankovich et al. |
| 6,283,956 | B1 * | 9/2001 | McDaniel ....................... 606/9 |
| 6,306,130 | B1 | 10/2001 | Anderson et al. ............. 606/27 |
| 6,402,739 | B1 * | 6/2002 | Neev .............................. 606/9 |
| 6,406,474 | B1 * | 6/2002 | Neuberger et al. ............. 606/9 |
| 6,569,156 | B1 | 5/2003 | Tankovich et al. |
| 6,605,080 | B1 | 8/2003 | Altshuler et al. ............... 606/3 |
| 6,613,040 | B2 | 9/2003 | Tankovich et al. |
| 6,613,042 | B1 | 9/2003 | Tankovich et al. |
| 6,632,219 | B1 | 10/2003 | Baranov et al. |
| 2002/0099094 | A1 | 7/2002 | Anderson ................... 514/561 |
| 2002/0169442 | A1 | 11/2002 | Neev |
| 2002/0173833 | A1 | 11/2002 | Korman et al. |
| 2002/0183724 | A1 | 12/2002 | Neev |
| 2002/0183789 | A1 | 12/2002 | Neev |
| 2003/0004501 | A1 | 1/2003 | Wilkens et al. |

OTHER PUBLICATIONS

Anderson et al., (1983) "Selective Photothermolysis: Precise Microsurgery by Selective Absorption of Pulsed Radiation" *Science*, 220(4596):524–527.

Blankenhorn, (1960) "The Infiltration of Cartenoids Into Human Atheromas and Xanthomas" *Annals of Internal Medcine*, 53(5):944–954.

Choi et al., "Acne Fulminans and 13–Cis–Retinoic Acid" *The Journal of Dermatology*, 19(6):378–383.

Elsner, (1995) "Sebum" in *Bioengineering of the Skin: Methods and Instrumentation*, eds. CRC Press Boca Raton, FL, pp. 81–89.

Gonzalez et al., (1992) "Treatment of Telangiectases and Other Benign Vascular Lesions with the 577 nm Pulsed Dye Laser" *Therapy*, 27(2):220–226.

Greenberg et al., (1990) "A Clinical Trial of Beta–Carotene to Prevent Basal Cell and Squamous Cell Cancers of the Skin" *New England Journal of Medicine*, 323(12):825–827.

Hosokawa et al., (1987) "Treatment of Large Xanthomas by the Use of Blepharoplasty Island Musculocutaneous Flaps" *Annals of Plastic Surgery*, 18(3):238–240.

Hunt et al., (1992) "A Comparative Study of Gluconolactone Versus Benzoyl Peroxide in the Treatment of Acne" *The Australasian Journal of Dermatology*, 33(3):131–134.

Ito et al., (1985) "Sebaceous Gland Hyperplasia on Rabbit Pinna Induced by Tetradecane" *The Journal of Investigative Dermatology*, 85(3):249–254.

Kuligowski et al., (1992) "Xanthoma Disseminatum" *International Journal of Dermatology*, 31(4):281–283.

Leyden, (1995) "New Understanding of the Pathogenesis of Acne" *The Journal of the American Academy Dermatology*, 32(5):S15–S23.

Lippman et al., (1993) "Comparison of Low–Dose Isotretinoin with Beta Carotene to Prevent Oral Carcinogenesis" *The New England Journal of Medicine*, 328(1):15–20, 57–59.

Mathews–Roth et al., (1977) "Beta Carotene Therapy for Erythropoietic Protoporphyria and Other Photosensitivity Diseases" *Archives of Dermatology*, 113(9):1229–1232.

Micozzi et al., (1988) "Cartenodermia in Men with Elevated Cartenoid Intake from Foods and β–Carotene Supplements" *The American Journal of Clinical Nutrition*, 48(4):1061–1064.

Nelson et al., (1996) "Dynamic Epidermal Cooling in Conjunction with Laser–Induced Photothermolysis of Port Wine Blood Vessels" *Lasers in Surgery and Medicine*, 19(2):224–229.

Ngim, (1992) "The Burned Ear (I): An Experimental Study with the Rabbit Model to Evaluate Scalding Temperature, Surface and Histopathologic Appearance, and Healing Responses with Depth of Injury" *Annals Academy of Medicine Singapore*, 21(5):597–604.

Nicolaides, (1974) "Skin Lipids: Their Biochemical Uniqueness" *Science* 186(4158):19–26.

Orfanos et al., (1998) "Oral Retinoids in the Treatment of Seborrhoea and Acne" *Dermatology*, 196(1):140–147.

Pearce et al., (1995) "Rate Process Analysis of Thermal Damage" in *Optical–Thermal Response of Laser–Irradiated Tissue*, eds. Welch, A.J. and Van Gemert, M.J.C. Plenum Press, NY, pp. 561–606.

Pinkus, (1974) "Sebaceous Glands and Acne Vulgaris: Unsolved Problems" *The Journal Investigative Dermatology*, 62(3):336–339.

Poblet et al., (1991) "Cystic verruciform xanthoma" *Journal of the American Academy of Dermatology*, 25(2):330–331.

Prince et al., (1988) "Increased Preferential Absorption Human Atheroslcerotic Plaque with Oral Beta Carotene" *Circulation*, 78(2):338–344.

Prince et al., (1991) "Rapid Serum Carotene Loading with High–Dose β–Carotene: Clinical Implications" *The Journal of Cardiovascular Pharmacology*, 17(2):343–347.

Prince et al., (1993) "Beta–Carotene Accumulation in Serum and Skin 1–3" *The American Journal Clinical Nutrition*, 57(2):175–181.

Shahidullah et al., (1994) "Isotretinoin Therapy in Acne Vulgaris: A 10–Year Retrospective Study in Singapore" *International Journal of Dermatology*, 33(1):60–63.

Shapiro et al., (1984) "Kinetic Caracteristics of β–Carotene Uptake and Depletion in Rat Tissue" *The Journal of Nutrition*, 114(10):1924–1933.

Sherwood et al., (1989) "Effect of Wavelength on Cutaneous Pigment Using Pulsed Irradiation" *The Journal of Investigative Dermatology*, 92(5):717–720.

Soong et al., (1991) "Nodular Lesions on the Face and Trunk. Xanthoma Disseminatum (XD)" *Archives of Dermatology*, 127(11):1717–1722.

Stathakis et al., (1997) "Descriptive Epidemiology of Acne Vulgaris in the Community" *Australian Journal of Dermatology*, 38(3):115–123.

Stewart, (1992) "Sebaceous Gland Lipids" *Seminars in Dermatology*, 11(2):100–105.

Strauss, (1976) "The Sebaceous Glands: Twenty–Five Years of Progress" *The Journal Investigation Dermatology*, 67(1):90–97.

Sykes, (1994) "Acne: A Review of Optimum Treatment" *Drugs*, 48(1):59–70.

Thomsen, (1991) "Pathologic Analysis of Photothermal and Photomechanical Effects of Laser–Tissue Interactions" *Photochemistry and Photobiology*, 53(6):825–835.

Tosti, (1974) "A Comparison of the Histodynamics of Sebaceious Glands and Epidermis in Man: A Microanatomic and Morphometric Study" *The Journal of Investigative Dermatology*, 62(3):147–152.

Turkington et al., (1996), "Skin Deep: An A–Z of Skin Disorders, Treatment and Health" *Facts on File, Inc.*, New York, pp. 7–9.

Weaver et al., (1969) "Mathematical Model of Skin Exposed to Thermal Radiation" *Aerospace Medicine*, 40(1):24–30.

Weinstein, (1974) "Cell Kinetics of Human Sebaceous Glands" *The Journal of Investigative Dermatology*, 62(3):144–146.

Welch et al., (1989) "Clinical Use of Laser–Tissue Interactions" *IEEE Engineering in Medicine and Biology Magazine*, pp. 10–13.

Williford et al., (1993) "The Spectrum of Normolipemic Plane Xanthoma," *The American Journal of Dermatopathology*, 15(6):572–575.

"New Prespectives on Acne," *Clinician*, Jul. 1994, 12(2):3–29.

Ceburkov et al. (2000) "Photodynamic Therapy in Dermatology" *Eur. J. Dermatol.* 10: 568–576.

Hongcharu et al. (2000) "Topical ALA–Photodynamic Therapy for the Treatment of Acne Vulgaris" *J. Invest. Dermatol.* 115: 183–192.

Itoh et al. (2001) "Photodynamic Therapy of Acne Vulgaris with Topical δ–aminolaevulinic Acid and Incoherent Light in Japanese Patients" *Brit. J. of Dermatol.* 144: 575–579.

Kalka et al. (2000) "Photodymamic Therapy in Dermatology" *J. Am. Acad. Dermatol.* 42: 389–413.

Karrer et al., (1999) "Long–pulse Dye Laser for Photodynamic Therapy: Investigations in Vitro and in Vivo" *Lasers Surg. Med.* 25: 51–59.

Sternberg et al. (1998) "Porphyrin–based Photosensitizers for Use in Photodynamic Therapy" *Tetrahedron* 54: 4151–4202.

Fournier et al., (2002) "Nonablative Remodeling: A 14–Month Clinical Ultrasound Imaging and Profilometric Evaluation of a 1540 nm Er:Glass Laser," *Dermatol Surg*, 28:926–931.

Levy et al., (2002) "Determination of Optimal Parameters for Laser for Nonablative Remodeling with a 1.54 μm Er:Glass Laser: A Dose–Response Study," *Dermatol Surg*, 28:405–409.

Lupton et al., (2002) "Nonablative Laser Skin Resurfacing using a 1540 nm Erbium Glass Laser: A Clinical and Histologic Analysis," *Dermatol Surg*, 28:833–835.

Mordon et al., (2000) "In Vivo Experimental Evaluation of Skin Remodeling by Using an Er:Glass Laser With Contact Cooling," *Lasers in Surgery and Medicine*, 27:1–9.

http://www.quantel–medical.fr/US/produits/ficheProduit.php?idProd=20.

Mehrtens, "The Interaction of Light with Skin," University of Canterbury, New Zealand, Masters Thesis, 1994.

Mehrtens, "Photothermal Treatment of Cutaneous Lesions," University of Canterbury, New Zealand, Doctor of Philosophy Thesis, 2001.

Zhang, "High Power Flashlamps in Dermatology," University of Canterbury, New Zealand, Masters Thesis, 1993.

* cited by examiner

METHOD OF TREATING DISORDERS ASSOCIATED WITH SEBACEOUS FOLLICLES

CROSS REFERENCE TO RELATED CASE

This application claims priority to and the benefit of Provisional U.S. Patent Application Serial No. 60/170,244, filed Dec. 10, 1999, the entirety of which is hereby incorporated herein by reference.

FIELD OF THE INVENTION

The invention relates generally to a method of treating a mammalian skin disorder associated with sebaceous follicles. More particularly, the invention relates to a method of treating acne in a mammal using a beam of laser or incoherent radiation.

BACKGROUND OF THE INVENTION

There are a variety of disorders associated with sebaceous follicles (also referred to herein as sebaceous follicle disorders) known to afflict mammals, in particular, humans. The disorders usually are associated with aberrations (for example, structural or functional aberrations) of the sebaceous follicles. In humans, sebaceous follicles, although present over most of the body surface, usually are largest and most dense on the face, chest and upper back. Accordingly, sebaceous follicle disorders predominantly affect these areas of the human body.

Probably the most pervasive sebaceous follicle disorder in the United States is acne, which affects between 40 to 50 million individuals in the United States (White G M, (1998) "Recent findings in the epidemiologic evidence, classification, and subtypes of acne vulgaris," J. AM. ACAD. DERMATOL. 39(2 Pt 3): S34–7). Acne occurs with greatest frequency in individuals between the ages of 15 and 18 years, but may begin at virtually any age and can persist into adulthood. In the 12 to 17-year old range, the incidence has been reported to be 25% (Strauss J S, (1982) "Skin care and incidence of skin disease in adolescence," CURR. MED. RES. OPIN. 7(Suppl 2):33–45). Acne is a disorder characterized by inflammatory, follicular, papular and/or pustular eruptions involving the sebaceous follicles (Stedman's Medical Dictionary, 26$^{th}$ edition, (1995) Williams & Wilkins). Although there are a variety of disorders that fall within the acne family, for example, acne conglobata, acne rosacea, and acne vulgaris, acne vulgaris probably is the most notable and commonly known form of acne. Acne vulgaris occurs with greatest frequency in individuals between the ages of 15 and 18 years, but may begin at virtually any age and can persist into adulthood. Because acne vulgaris can lead to permanent scarring, for example, facial scarring, this form of acne can have profound and long-lasting psychological effects on an afflicted individual. Furthermore, pustule formation and scarring can occur at an age when the potential impact on an individual is greatest. As a result, enormous amounts of money (i.e., on the order of billions of dollars) are spent annually in the United States on various topical and systemic acne treatments. These treatments often are employed without the guidance or supervision of a physician.

Acne vulgaris typically results from a blockage of the opening of the sebaceous follicle. It is believed that both (i) the amount of sebum, a lipid, keratin and cellular debris containing fluid, produced and secreted by the sebaceous glands and (ii) bacteria, namely, *Propionibacterium acnes* (*P. acnes*) which metabolize lipids in the sebum, play a role in formation and development of acne vulgaris. The basic lesion of acne vulgaris is referred to as a comedo, a distension of the sebaceous follicle caused by sebum and keratinous debris. Formation of a comedo usually begins with defective keratinization of the follicular duct, resulting in abnormally adherent epithelial cells and plugging of the duct. When sebum production continues unabated, the plugged follicular duct distends. A blackhead (or open comedo) occurs when a plug comprising a melanin containing blackened mass of epithelial debris pushes up to opening of the follicular duct at the skin surface. A whitehead (or closed comedo) occurs when the follicle opening becomes very tightly closed and the material behind the closure ruptures the follicle causing a low-grade dermal inflammatory reaction. Accordingly, some comedones, for example, in acne vulgaris, evolve into inflammatory papules, pustules, nodules, or chronic granulomatous lesions. Proliferation of *P. acnes* can result in the production of inflammatory compounds, eventually resulting in neutrophil chemotaxis (Skyes and Webster (1994) Drugs 48: 59–70).

At present, acne patients may receive years of chronic topical or systemic treatments. Current treatment options include, for example, the use of topical anti-inflammatory agents, antibiotics and peeling agents, oral antibiotics, topical and oral retinoids, and hormonal agonists and antagonists. Topical agents include, for example, retinoic acid, benzoyl peroxide, and salicylic acid (Harrison's Principles of Internal Medicine, 14$^{th}$ edition, (1998) Fauci et al., eds. McGraw-Hill). Useful topical antibiotics include, for example, clindamycin, erythromycin, and tetracycline and useful systemic antibiotics include, for example, erythromycin, tetracycline, and sulphanilamides (see, for example, U.S. Pat. Nos. 5,910,493 and 5,674,539). Administration of the systemic retinoid, isotretinion, has demonstrated some success in the treatment of acne (Harrison's Principles of Internal Medicine, 14$^{th}$ edition, (1998) Fauci et al., eds. McGraw-Hill). Studies indicate that this drug decreases sebaceous gland size, decreases the rate of sebum production and/or secretion, and causes ductal epithelial cells to be less adherent, thereby preventing precursor lesions of acne vulgaris (Skyes and Webster (1994) supra). Side-effects, however, include dry mouth and skin, itching, small red spots in the skin, and eye irritation. A significant concern about oral retinoids is their possible teratogenicity (Turkington and Dover (1996) SKIN DEEP: AN A–Z OF SKIN DISORDERS, TREATMENT AND HEALTH FACTS ON FILE, Inc., New York, page 9). In addition, a variety of hormone-related, for example, corticosteroid anti-inflammatory therapies have been developed for the treatment of acne. These therapies can be expensive and most are associated with deleterious systemic or localized side-effects (Strauss (1982) "Skin care and incidence of skin disease in adolescence," CURR. MED. RES. OPIN. 7(Suppl 2): 33–45).

Because the foregoing therapies generally do not affect the structure and/or function of sebaceous follicles associated with the disease, the treatments remain non-curative. In other words, the disorder may recur after cessation of therapy. The result can be years of chronic therapy, and potential scarring for the patient, and enormous associated health care costs.

In recent years, a variety of laser-based methodologies for treating acne have been developed. The methods generally involve the combination of laser radiation and either an exogenous or endogenous chromophore present in the target tissue so that the laser light is absorbed preferentially in the target tissue causing morphological changes to the sebaceous follicle and/or causing a reduction of sebum production. For example, U.S. Pat. No. 5,817,089 describes a laser-based method for treating acne requiring topical application of a light absorbing chromophore, for example, 5 micron graphite particles dispersed in mineral oil, onto skin needing such treatment. Similarly, U.S. Pat. No. 5,304,170 also describes a laser-based method for treating acne in which target cells contain greater amounts of a light absorbing chromophore, for example, the carotenoid β-carotene, relative to lesser or non-pigmented surrounding cells. In the chromophore based methods it can be difficult to get sufficient chromophore in the target region to elicit selective tissue damage and the method may still damage the outer layers of the skin resulting in scarring.

SUMMARY OF THE INVENTION

The present invention addresses the foregoing problems and provides a method for treating sebaceous follicle disorders of mammalian skin, for example, human skin. The method permits treatment of the sebaceous follicle disorder while at the same time preserving surrounding skin tissue, for example, skin epidermis. The invention offers numerous advantages over existing treatment protocols. For example, the method provides a long lasting treatment which persists long after treatment has ceased. Furthermore, the method minimizes trauma and scar formation at the skin surface, reduces side-effects, such as, pain, erythema, edema, and blistering, which can result from other treatments, and can also minimize pigmentary disturbances of the skin.

In one aspect, the present invention features a method of treating a sebaceous follicle disorder in a preselected region of mammalian skin, the preselected region having at least one lesion characteristic of the disorder disposed therein. The method comprises the steps of (a) cooling an exposed surface of the preselected region of the mammalian skin and (b) applying heating energy to the preselected region in an amount sufficient to ameliorate the lesion disposed within the preselected region. Without wishing to be bound by theory, it is contemplated that amelioration of the lesion can result from the destruction of the sebaceous follicle, structural changes to the sebaceous follicle to reduce the possibility of pore blockage, and/or reduction of sebum production by the sebaceous gland associated with the sebaceous follicle. As will be discussed in more detail below, the cooling step can be performed prior to and/or contemporaneous with the step of applying the heating energy. Furthermore, it is contemplated that the cooling step can be performed after the heating step.

In a preferred embodiment, the heating energy is provided by means of a beam of radiation (for example, coherent or incoherent radiation), microwaves, ultrasound or radio frequency (RF) current. More preferably, the heat energy originates from a source of radiation, and most preferably from a source of coherent radiation. The source of the coherent radiation can be, for example, a pulsed, scanned, or gated continuous wave (CW) laser.

In a preferred embodiment, the beam of radiation comprises a wavelength in the range from about 0.6 microns to about 1.8 microns, more preferably in the range from about 1.2 to about 1.6 microns, and more preferably in the range from about 1.3 to about 1.6 microns. Most preferably, the beam has a nominal wavelength of about 1.5 microns. The beam preferably has either a fluence in the range from about 5 to about 500 joules per square centimeter, and more preferably in the range from about 10 to about 150 joules per square centimeter, or a power density in the range of about 1 to about 10,000 watts per square centimeter, and more preferably in the range from about 5 to about 5,000 watts per square centimeter.

During practice of the invention, application of the heating energy can induce thermal changes to the portion of the dermis where sebaceous follicles reside. This heating may result in the destruction of the sebaceous follicle or the sebaceous gland associated with the follicle, cause structural changes in the follicle to reduce the likelihood of blockage and/or reduce the level of sebum production. The cooling step serves to preserve the epidermis and the dermis overlaying the sebaceous gland containing region of the skin thereby reducing side-effects such as pain, erythema, edema, and blistering which otherwise may result from exposure to the beam of radiation. The cooling step can be performed prior to, contemporaneous with, or after application of the energy to the target region, or alternatively the cooling can result from a combination of such cooling steps.

Cooling can be achieved using many different techniques known and used in the art. For example, cooling can be achieved by blowing a stream of cold air or gas onto the target site, by applying a cold liquid onto the target site, by conductive cooling using a cold contact surface applied to the target site, or by evaporative cooling using a low boiling point liquid applied to the target tissue. In a preferred embodiment, cooling is achieved using evaporative cooling technologies by means of, for example, a commercially available dynamic cooling device (DCD).

Practice of the invention can be prophylactic or can be performed to ameliorate one or more symptoms or lesions associated with the various sebaceous follicle disorders. Exemplary sebaceous follicle disorders include, for example, acne vulgaris, acne rosacea, acne conglobata, seborrhea, sebaceous adenoma and sebaceous gland hyperplasia. The present invention, however, is particularly useful in the treatment of acne, more specifically, the treatment of acne vulgaris.

Sebaceous follicle disorders, for example, acne vulgaris and seborrhea, sometimes are associated with the overproduction of sebum. For example, in acne vulgaris, the level of sebum production by sebaceous glands has been correlated with the severity of the disorder (Leyden (1995) J. AM. ACAD. DERM. 32: S15–25). Accordingly, in a preferred embodiment, the method of the invention lowers or even eliminates sebum production by sebaceous glands of sebaceous follicles relative to untreated sebaceous follicles. In another embodiment, treatment can increase the size of the opening of the sebaceous follicle, in the proximity of the infundibulum, thereby affecting sebum flow and/or minimizing the likelihood of blockage of the sebaceous follicle. Furthermore, treatment may destroy or inactivate the sebaceous follicle thereby eliminating sebum production in that follicle.

Application of the heating energy can reduce the size of one or more lesions, for example, comedones in the case of acne vulgaris, disposed within the preselected region. Furthermore, application of the heating energy can also reduce the density of the lesions disposed within the preselected region. In cases in which skin inflammation can be associated with the lesion, for example, in severe cases of acne vulgaris and acne conglobata, the application of the heating energy may reduce the inflammation associated with the lesion. The benefit of treatment, for example, reduction in the number of or elimination of skin lesions, may become apparent days to weeks after the treatment. Furthermore, it is contemplated that in certain cases, e.g., severe cases, of sebaceous follicle disorders, multiple rounds of treatment, for example, two to ten separate rounds of treatment, may be required to treat an individual satisfactorily.

It is contemplated that, based upon choice of appropriate cooling and/or heat energy parameters, it is possible to create thermally induced changes of sebaceous follicles in the absence of an exogenous energy absorbing material. However, under some circumstances, for example, when heating is accomplished by the application of a radiation beam, optimal treatment may be facilitated by applying to the preselected region prior to exposure to the radiation beam a radiation absorbing material, for example, a chromophore photoexcited by the radiation. The radiation absorbing material may be administered systemically to the mammal or applied topically to the preselected region prior to exposure to the radiation beam.

BRIEF DESCRIPTION OF THE DRAWINGS

The foregoing and other objects, features and advantages of the invention will become apparent from the following description of preferred embodiments of the invention, as illustrated in the accompanying drawings. Like referenced elements identify common features in corresponding drawings. The drawings are not necessarily to scale, with emphasis instead being placed on illustrating the principles of the present invention, in which.

DETAILED DESCRIPTION OF THE INVENTION

The present invention is based, in part, upon the discovery that it is possible to treat sebaceous follicle disorders while at the same time preventing or minimizing damage to skin tissue surrounding sebaceous follicles afflicted with the disorder. In particular, sebaceous follicles and dermal regions containing sebaceous follicles are targeted for heat injury whereas the underlying dermal and overlaying dermal and epidermal regions are protected from thermal injury. The underlying dermal regions are protected from thermal injury because, by selection of appropriate parameters, it is possible to limit the penetration depth of the heating applied to the region. Accordingly, by choice of appropriate parameters it is possible to heat skin tissue to a preselected depth thereby sparing the underlying tissue from thermal injury. The overlaying dermal and epidermal regions are protected from thermal injury by appropriate surface cooling. Accordingly, by choice of appropriate heating and cooling parameters it is possible for the skilled artisan to induce thermal injury to a specific target zone within the dermis of the skin.

The method of the invention is comprised primarily of two steps. In one step, an exposed surface of a preselected region of mammalian skin having at least one lesion characteristic of a sebaceous follicle disorder is cooled. In a second step, heating energy, for example, radiation, is applied to the preselected region in an amount and for a time sufficient to induce thermal damage to a portion of the skin containing a sebaceous follicle thereby to reduce or eliminate the production of sebum in the sebaceous follicle or to alter the structure of the sebaceous follicle, for example, by increasing the internal diameter of the follicle, to minimize the possibility of blockage of the follicle. As a result, the treatment ameliorates one or more skin lesions associated with the sebaceous follicle disorder while at the same time preserving the surface of the skin exposed to the heating energy.

Figure 1:
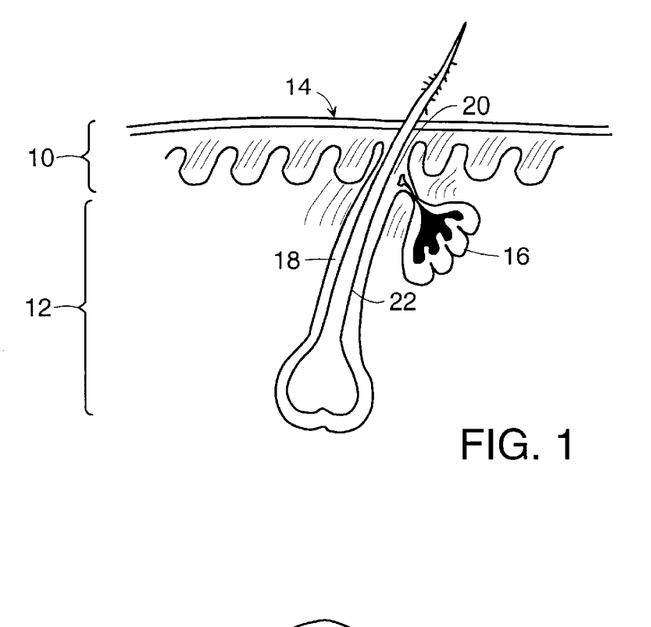
FIG. 1 is a schematic representation of a vertical cross section of a sebaceous follicle disposed within mammalian skin.

FIG. 1 is a schematic illustration of a cross-sectional view of a sebaceous follicle disposed within human skin. Skin is comprised primarily of two layers in which the top layer of skin, known as the epidermis 10, is supported by a layer known as the dermis 12. The epidermis 10, has an exposed surface 14. In human skin, epidermis 10 extends to a depth of about 60–100 microns from skin surface 14 whereas the underlying dermis 12 extends to a depth of about 4 to 5 millimeters from the skin surface 14. Furthermore, in skin, dermis 12 is supported by or is disposed upon a layer of subcutaneous fat (not shown). Dermis 12 is primarily acellular and comprises primarily water, collagen, and glycosaminoglycans. Water constitutes approximately 60–80 percent of the total weight of the dermis.

As shown, sebaceous gland 16 is in fluid flow communication with a hair duct 18. As a result, sebum produced by the sebaceous gland 16 flows into the hair duct 18. The upper portion of hair duct 18 which receives sebum from sebaceous gland 16 is referred to as the infundibulum 20. Hair shaft 22 is disposed within hair duct 18 and extends beyond the surface of the skin 14. Sebaceous glands usually are located at depths ranging from about 200 to about 1000 microns from the skin surface (Conontagna et al. (1992) in "ATLAS OF NORMAL HUMAN SKIN" by Springer Verlag, New York, N.Y.).

At birth, sebaceous follicles typically contain a small hair, a follicular orifice lined with epithelial cells, and a sebaceous gland. The outer layer of the sebaceous gland lobule is composed of undifferentiated hormonally responsive cells. In response to androgens, these cells, called sebocytes, divide and differentiate. Lipids accumulate and the cells enlarge and rupture, releasing their contents into the hair duct. Sebum, the product of the sebaceous gland, is composed of lipids and cellular debris combined with keratin and microorganisms, including the bacterium *P. acnes* (Sykes and Webster (1994) supra). Sebaceous glands and the sebum they produce have no proven function in humans, and in fact the skin of young children does not appear to be negatively affected by the almost lack of sebum (Staruss et al. (1992), J. INVEST. DERM., 67:90–97, and Stewart, M. E., (1992) SEMINAR. DERM. 11, 100–105).

As used herein, the term "sebaceous follicle" refers to any structure disposed within mammalian, particularly, human, skin, which comprises a hair follicle, also referred to herein as a hair duct, attached to and in fluid flow communication with a sebaceous gland. As a result, sebum produced by the sebaceous gland flows into the hair follicle. The sebaceous follicle optionally may include a hair shaft disposed within the hair follicle. As discussed, the upper portion of the hair follicle into which sebum is released from the sebaceous gland is referred to as the infundibulum.

As used herein, the term "sebaceous follicle disorder" refers to any disorder of mammalian skin, in particular, human skin, that is associated with a sebaceous follicle. Sebaceous follicle disorders can result from an over production of sebum by a sebaceous gland of a sebaceous follicle and/or reduction or blockage of sebum flow in the infundibulum of the sebaceous follicle. Exemplary sebaceous gland disorders include, for example, acne, for example, acne vulgaris, acne rosacea, and acne conglobata, seborrhea, sebaceous adenoma and sebaceous gland hyperplasia.

As used herein, the term "lesion characteristic of the disorder" refers to any skin lesion associated with the sebaceous follicle disorder. For example, lesions associated with acne may include, without limitation, papules and pustules, and skin inflammation associated with the papules and pustules. In addition, specific lesions of acne conglobata include cystic lesions, abscesses and communicating sinuses, whereas specific lesions of acne vulgaris include comedones, cysts, papules and pustules on an inflammatory base. Lesions associated with seborrhea include, without limitation, dermatitis and eczema.

As used herein, the term "ameliorate a lesion" refers to a decrease in the size of a sebaceous follicle disorder-associated lesion and/or density of sebaceous follicle disorder-associated lesions in a preselected region, and can also include a decrease in skin-inflammation associated with the sebaceous follicle disorder.

As used herein, the terms "thermal change" or thermal injury" with reference to sebaceous follicles refers to any change, for example, structural change and/or functional change, to the sebaceous follicle which ameliorates one or more lesions associated with the sebaceous gland disorder. For example, sebum over-production can be a factor associated with certain sebaceous follicle disorders. Accordingly, practice of the method of the invention can reduce sebaceous gland size and/or sebum production in the area afflicted with the disorder. Reduction in sebum production can occur when sebum producing cells disposed within the sebaceous glands are destroyed and thus inactivated, or when their sebum producing activity is reduced. Furthermore, practice of the method of the invention may result in morphological changes to the sebaceous follicle, for example, increasing the diameter of the follicle, to minimize the likelihood of plug formation. Accordingly, in this type of situation it is possible that, by enlarging the size of the follicle, the chance of plug formation is reduced so that any sebum produced by the sebaceous gland can still flow out of the sebaceous follicle. The changes are thermally induced and may result from the temperature-induced cell death and/or protein denaturation. Accordingly, an objective of the method is to elevate the temperature of the dermal region containing sebaceous glands and more specifically the sebaceous gland to a level and for a time sufficient to cause cell death and/or protein denaturation.

A variety of methods useful in measuring sebum production and useful in the practice of the invention are thoroughly documented in the art. For example, the level of sebum production can be measured by using commercially available sebutape or by means of a sebumeter.

Sebutape is a microporous patch available from CeDerm Corporation (17430 Campbell Rd., Dallas, Tex. 75252). Sebutape detects sebum production without the use of any solvents, powders, or chemicals. The microporous patch acts as a passive collector of sebum. Gradual displacement of air in the pores of the patch changes the patches appearance. The sebum filled pores in the patch do not scatter light and thus appear transparent. The size of the transparent area is a measure of the amount of sebum collected. Patches can be placed on a dark background storage card for evaluation by eye or by computer imaging (Elsner (1995) in "BIOENGINEERING OF THE SKIN: METHODS AND INSTRUMENTATION," Berardesca, et al., eds., 81–89, CRC Press, Boca Raton, Fla.).

In addition to sebutape, sebum production can be measured by means of a device referred to in the art as a sebumeter, for example, a model SM 810 PC sebumeter, obtainable from Courage & Khazaka (Mathias-Bruggen Str. 91, Koln, Germany). A sebumeter measures the content of sebum in the stratum corneum of skin, the values of which are expressed in micrograms/cm$^2$. The sebumeter can be fitted with a manual data collector which has a band designed to absorb skin sebum. The band is 0.1 mm thick and has a 64 mm$^2$ contact surface. The higher the amount of lipids present in the band, the higher the film transparency. The numeric values shown on the display are directly proportional to the band transparency and thereby to the amount of lipids present in the band itself (Elsner (1995) supra and http://www.corage-khazaka.de/products.htm and Clarys and Barel (1995) Quantitative Evaluation of Skin Surface Lipids, CLINICS IN DERMATOLOGY 13: 307–321).

Heating of the dermal region may be accomplished by applying to the skin any energy source capable of heating living tissue to a depth where sebaceous follicles are located. Heating energy can be provided by, for example, coherent light, incoherent light, microwaves, ultrasound or RF current. The energy, however, preferably is provided via a radiation beam of coherent or incoherent light. Coherent light sources, however, are more preferred. Coherent light sources useful in the practice of the invention include, but are not limited to, pulsed, scanned or gated CW lasers.

Figure 2:
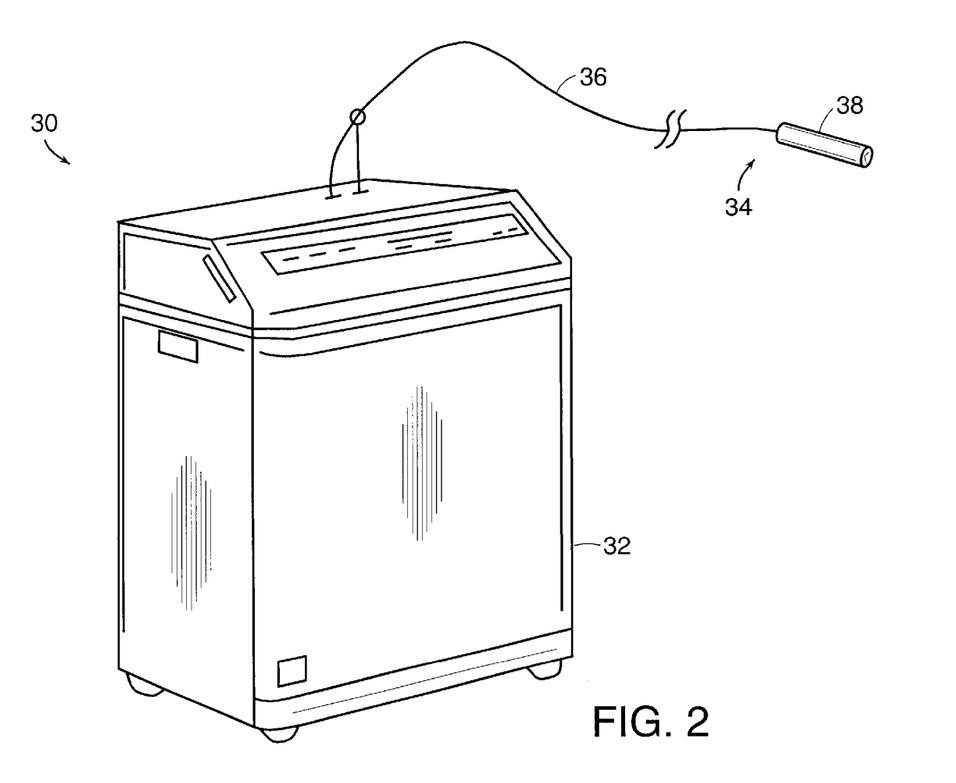
FIG. 2 is a schematic representation of an apparatus including a radiation source and delivery system useful in the practice of the invention.

FIG. 2 is an illustration of a system 30 useful in the practice of the invention. The system 30 includes an energy source 32 and a delivery system 34. A beam of energy generated by the energy source 32 is directed to a target region of the individuals skin afflicted with the sebaceous follicle disorder via delivery system 34. The delivery system 34 comprises a fiber 36 having a circular cross-section and a hand piece 38. The energy beam having a circular cross-section is delivered by fiber 36 to the hand piece 38. An optical system within the handpiece 38 projects an output beam of energy to the target region of the skin. A user holding the handpiece 38 can irradiate the target region of the skin with the output beam. In a preferred embodiment, energy source 32 is a laser that can produce a beam of pulsed, scanned or gated CW laser radiation. With regard to the radiation beam, it is contemplated that the wavelength of the beam may be optimized by routine experimentation to maximize absorption by the sebaceous glands and or by the dermis layer of skin where sebaceous glands typically reside.

In another embodiment, the radiation beam used to thermally injure the sebaceous glands and/or the dermal tissue can originate from a compact, handheld device consisting of a diode laser alone or in combination with additional apparatus such as an optical fiber, doped in such a way so as to delivery energy at a wavelength and power level so as to be therapeutically effective.

The parameter ranges for the beam optimally are selected to cause thermal injury to the sebaceous glands and/or to portions of the dermis where the sebaceous glands typically are present while at the same time avoiding injury to the epidermis and surrounding dermal regions. In particular, the wavelength of the radiation beam can be chosen to maximize absorption by the targeted region of the dermis, and the fluence or power density, depending on the type of radiation, chosen to minimize treatment related side-effects, including, for example, erythema, hypopigmentation, hyperpigmentation, and/or edema. The wavelength range chosen has a tissue absorption coefficient preferably in the range of about 1 to about 50 cm$^{-1}$. Thus, the beam preferably has a wavelength of between about 0.6 to about 1.8 microns, more preferably has a wavelength of between about 1.2 to about 1.7 microns, and more preferably has a wavelength of between 1.3 to about 1.6 microns. In one embodiment, the radiation beam has a nominal wavelength of approximately 1.45 microns.

By choice of appropriate wavelengths it is possible to target selected zones within the dermis of the skin. Table 1 lists wavelength in nanometers versus penetration depth ($\delta$) in micrometers estimated using the formula:

$$\delta(\lambda)=1/\mu_{tr}(\lambda)$$

wherein $\mu_{tr}(\lambda)$ is given by the formula, $$\mu_{tr}(\lambda)=\mu_a(\lambda)+\mu_s'(\lambda)$$

wherein $\mu_{tr}(\lambda)$ is the wavelength dependent total transport attenuation coefficient, $\mu_a(\lambda)$ is the absorption coefficient, and $\mu_s'(\lambda)$ is the reduced scattering coefficient defined as, $$\mu_s'(\lambda)=\mu_s(\lambda)*(1-g(\lambda))$$

wherein $\mu_s(\lambda)$ is the single scattering coefficient and $g(\lambda)$ is the scattering anisotropy factor.

Values of $\mu_a(\lambda)$ and $\mu_s'(\lambda)$ were taken from Simpson et al. (1998) Phys. Med. Biol. 43(9):2465–78 and from measurements of water absorption for estimated typical skin hydration levels of between 60% and 80%.

TABLE 1

| Wavelength (nm) | Penetration Depth (microns) |
| --- | --- |
| 600 | 317 ± 35 |
| 650 | 339 ± 37 |
| 700 | 391 ± 37 |
| 750 | 437 ± 36 |
| 800 | 487 ± 34 |
| 850 | 530 ± 35 |
| 900 | 572 ± 37 |
| 950 | 602 ± 35 |
| 1000 | 624 ± 24 |
| 1330 | 865 ± 50 |
| 1450 | 326 ± 32 |
| 1550 | 590 ± 35 |

Lasers which produce radiation having wavelengths in the range of between about 0.6 and 1.8 microns include, for example, a 0.69 micron ruby laser, a 1.06 micron Nd:YAG laser, a 1.33 micron Nd:YAG laser, a 1.45 micron Nd:YAG laser, a 1.54 micron Er:Glass laser, and a diode laser with appropriate substrate and doping. The radiation beam may be pulsed, scanned or gated continuous wave laser radiation.

It is contemplated that therapeutically effective dosimitries for coherent sources, for example, pulsed sources, can range from about 5 to about 500 joules per square centimeter, more preferably in the range from about 10 to about 150 joules per square centimeter. Similarly, it is contemplated that therapeutically effective dosimitries for incoherent sources can range from about 1 to about 10,000 watts per square centimeter, more preferably in the range from about 5 to about 5,000 watts per square centimeter.

Minimization of thermal injury to the epidermis and the upper layers of the dermis can be accomplished by cooling the skin surface prior to, contemporaneous with, and/or after heating the sebaceous gland containing portion of the dermis. Furthermore, if the heating source is pulsed, cooling can be applied at intervals between the heating pulses. It is contemplated that the energy delivery system 34 also may include an integrated cooling system for cooling the skin surface prior to, contemporaneous with, and/or after the application of the energy beam. Accordingly, such an energy delivery system would be multi-functional, i.e., capable of both delivering an energy beam and cooling the surface of the skin at the same time.

Cooling may be facilitated by one or more cooling systems known and used in the art. Cooling systems useful in the practice of the invention may include, without limitation: blowing a cold stream of gas, for example, cold air, or cold $N_2$ or He gas, onto the surface of the skin (Sturesson and Andersson-Engels (1996) "Mathematical modelling of dynamic cooling and pre-heating, used to increase the depth of selective damage to blood vessels in laser treatment of port wine stains," PHYS. MED. BIOL. 41(3):413–28); spraying a cold liquid stream onto the surface of the skin (Sturesson (1996) supra); conductive cooling using a cold contact surface which does not interfere with the method of heating, for example, a cooled transparent optical material, such as a cooled sapphire tip, see, for example, U.S. Pat. No. 5,810,801; or by application of a low boiling point, non-toxic liquid, for example, tetrafluoroethane or chlorodifluoromethane, onto the surface of the target tissue, thereby cooling the tissue surface by evaporative cooling.

In a preferred embodiment, cooling is facilitated by a dynamic cooling device (DCD), such as a DCD manufactured by Candela Corporation. Applications of the DCD have been described in the art and include, for example, Anvari et al. (1996) APPLIED OPTICS 35:3314–3319; Anvari et al. (1997) PHYS. MED. BIOL. 42:1–18; Ankara et al. (1995) LASERS IN MEDICAL SCIENCE 10:105–112; and Waldorf et al. (1997) DERMATOL. SURG. 23:657–662, U.S. Pat. Nos. 5,820,626 and 5,814,040 and PCT/US97/03449. The DCD provides a timed spray of fluid onto the surface of the skin, prior to, contemporaneous with, and/or after the application of the energy beam. Unlike steady-state cooling, for example, an ice cube held against the tissue, dynamic cooling primarily reduces the temperature of the most superficial layers of the skin. For example, it has been estimated that the use of tetrafluoroethane as a cryogen may result in a drop in surface-temperature of about 30–40° C. in about 5–100 ms (see Anvari et al. (1991) supra).

Figure 3:
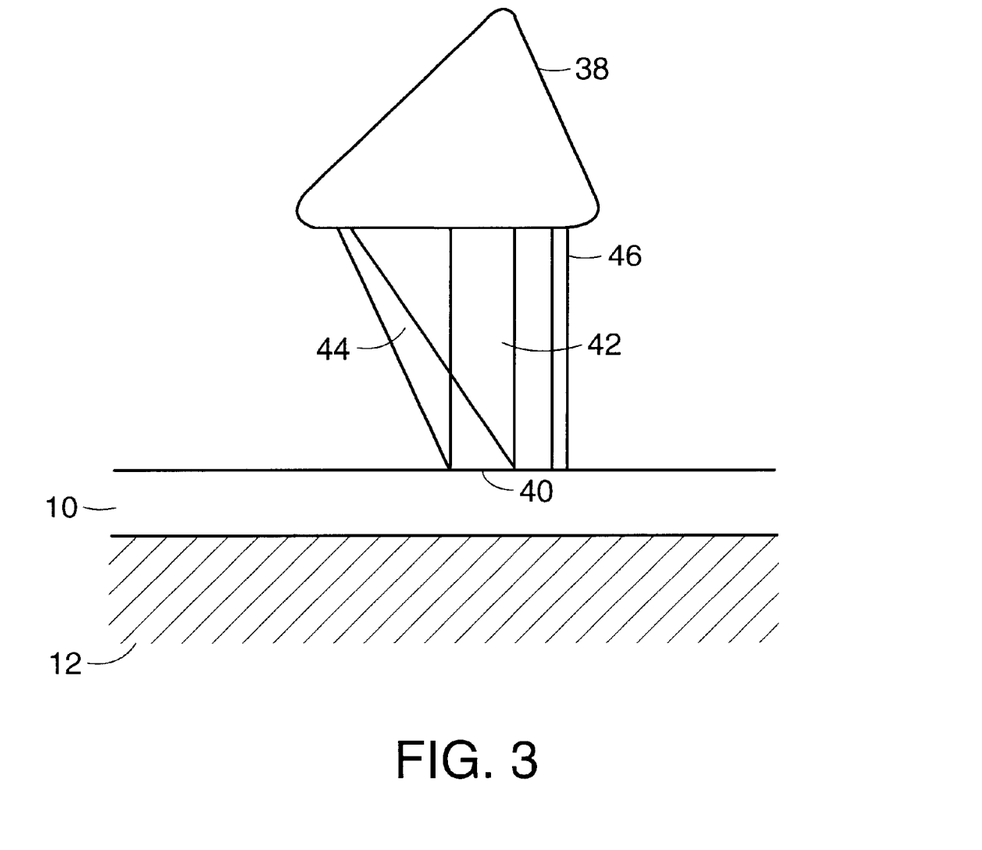
FIG. 3 is a schematic representation of an exemplary hand set of a delivery system in which a beam of coherent radiation and cryogen spray are applied to the same region of the skin surface.

Operation of such an embodiment is shown schematically in FIG. 3. Briefly, hand piece 38 is used to apply a beam of radiation 42 from a laser source and a cryogen spray 44 to preselected region 40 of the skin surface. Application of the heat energy together with surface cooling cause thermal injury to the sebaceous follicle containing portion of the dermis while preserving epidermis 10. Guide 46 ensures that the handpiece 38 is positioned at the appropriate height above the surface of the skin to ensure that the beam of radiation 42 and the cryogen spray 44 both contact skin surface at the preselected region 40.

Figure 4:
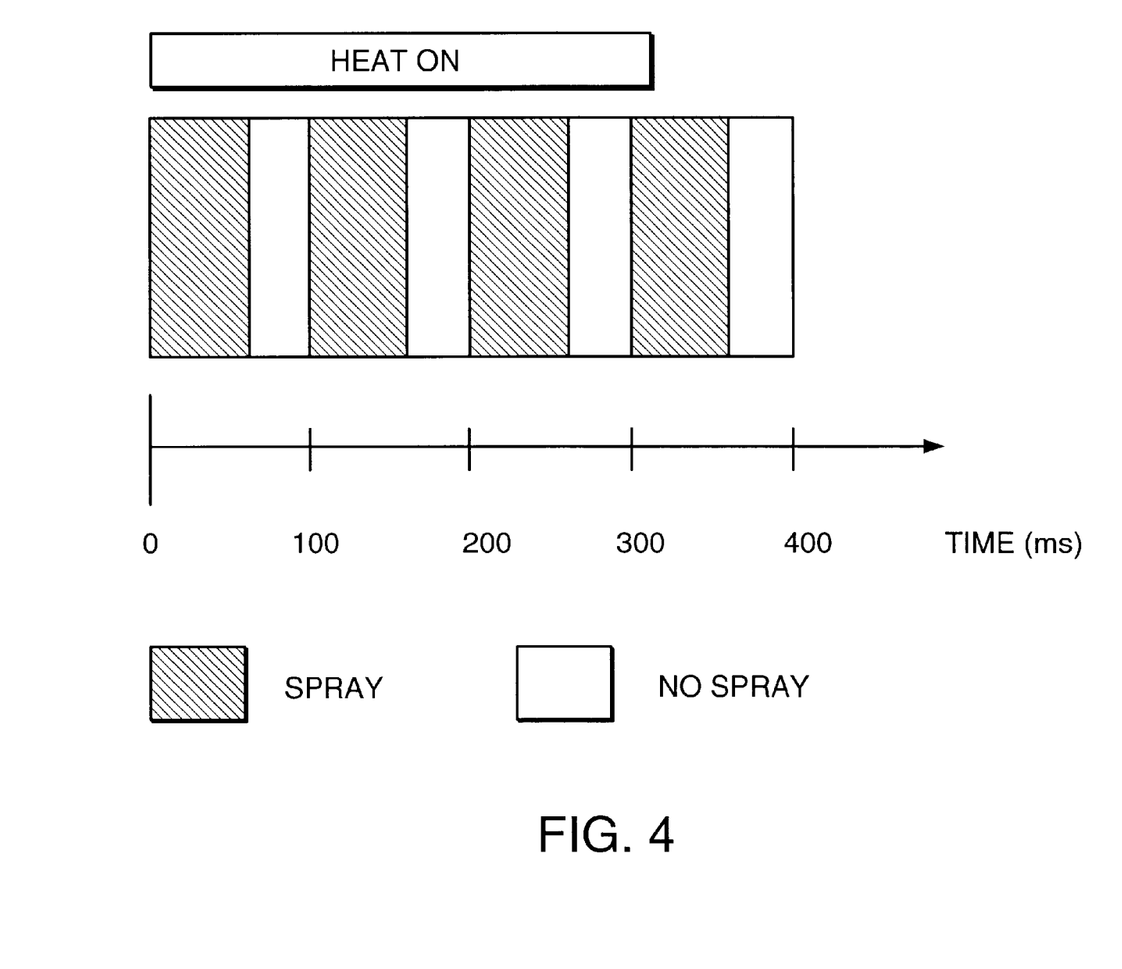
FIG. 4 is a schematic representation of an exemplary timing diagram showing exemplary heating and cooling phases useful in the practice of the invention.

FIG. 4 provides an exemplary timing diagram showing time phases for the heating and/or cooling of the skin tissue afflicted with the disorder. The heating phase, represented by the horizontal bar, has a duration of 300 ms. Cooling, represented by vertical bars, comprises four separate cycles having a duration of 100 ms, each cycle comprising a 70 ms period when cryogen spray is applied to the skin surface and a 30 ms period when no cryogen spray is applied to the skin surface. In this timing diagram, the skin surface is cooled both (i) at the same time (i.e., the 70 ms phases of the first three cooling cycles) as the skin is exposed to the radiation beam and (ii) after (i.e., the 70 ms phase of the fourth cooling cycle) the skin has been exposed to the radiation beam.

The preselected region can be cooled prior to, contemporaneous with, and even after the application of the energy beam. The relative timing of cooling the skin surface and the application of heating energy depends, in part, on the depth to which thermal injury is to be prevented. Longer periods of cooling prior to the application of radiation allow more time for heat to diffuse out of the tissue and cause a thicker layer of tissue to be cooled, as compared to the thickness of the layer cooled by a short period of cooling. This thicker layer of cooled tissue sustains less thermal injury when the heating energy is subsequently applied. Continued cooling of the skin surface during the delivery of heating energy extracts heat from the upper layers of the skin as heat is deposited, thereby further protecting the upper skin layers (e.g., epidermis and dermis overlaying the target region) from thermal injury.

In another embodiment, the energy delivery and cooling systems may comprise separate systems. The cooling system may comprise a container of a cold fluid. Cooling the surface of the skin can be accomplished by applying the cold fluid onto the skin which then extracts heat from the skin on contact. In such an embodiment, an energy delivery system comprises, for example, a handpiece containing optics for directing, collimating or focusing the radiation beam onto the targeting region of the skin surface. The radiation beam can be carried from the energy source, for example, a laser, to the handpiece by, for example, an optically transparent fiber, for example, an optical fiber. Coolant from a separate reservoir can be applied to the surface of the targeted region. In this embodiment, coolant from the reservoir flows to a dispensing unit separate from the energy delivery system via tubing connecting the reservoir and the dispensing unit. The coolant, once dispensed, can be retained in situ on the surface of the targeted region by a ring, for example, a transparent ring, which can be attached to the energy delivery system.

Selective heating of dermal regions containing the sebaceous glands can be achieved by selecting the appropriate heating and cooling parameters. For example, by choosing the appropriate wavelength it is possible to selectively heat portions of the dermis to a desired depth. For example, it is estimated that light having a wavelength of 1000 nm penetrates to a depth of approximately 600 microns. Accordingly, it is contemplated that dermal tissue greater than 600 microns from the skin surface will not be subjected to such intense heating as the region within 600 microns of the skin surface. Furthermore, it is possible to prevent damage to the skin surface by applying the types of cooling discussed hereinabove. By choosing appropriate parameters for the heating and cooling steps it is possible to selectively heat and thus selectively damage particular zones (target regions) within the skin which may contain a sebaceous gland and/or an infundibulum of a sebaceous follicle.

Specifically, by choosing the radiation wavelength, the timing of the surface cooling, the cooling temperature, the radiation fluence and/or the power density as described above, the depth, thickness and degree of thermal injury can be confined to a particular zone within the dermis. Optimization of the foregoing parameters can be used to selectively heat regions of the dermis containing sebaceous follicles, more preferably regions containing sebaceous glands, while at the same time substantially or completely sparing injury to overlying regions of epidermis and dermis as well as underlying layers of dermis.

Practice of the method of the invention preferably results in the targeted region of the dermis being heated to a temperature in the range from about 50° C. to about 85° C., and more preferably from about 60° C. to about 70° C. This temperature rise can be sufficient to affect the structure and/or function of sebaceous follicles disposed within the targeted region of the dermis. Studies have indicated that temperatures of 60° C. and above may be sufficient to create thermal damage to skin (Weaver & Stoll (1969) AEROSPACE MED 40: 24). The cooling system on the other hand, preferably cools the area of the skin above the targeted dermal region to temperatures below about 60° C., more preferably to below 50° C. during application of the heating energy, thereby minimizing or avoiding collateral thermal damage to the epidermis.

Although the method of the invention can treat sebaceous follicle disorders in the absence of an exogenously added energy absorbing material, under certain circumstances, it may be beneficial to introduce such a material into the targeted region prior to application of the heat energy. For example, where the energy source is a beam of coherent or incoherent radiation, an externally injected radiation absorber, for example, a non-toxic dye, for example, indocynanine green or methylene blue, can be injected into the targeted dermal region. A radiation source provides radiation which is absorbed by tissue containing the absorber. As a result, use of a radiation absorbing material in combination with surface cooling can confine thermal injury or damage to the targeted dermal regions thereby minimizing potential injury to surrounding tissue.

EXAMPLES

Practice of the invention will be more fully understood from the following examples, which are presented herein for illustrative purposes only, and should not be construed as limiting the invention in any way.

Example 1

Computer Modeling of Treatment Parameters

Mathematical calculations were performed to determine whether certain heating and cooling schemes could produce the desired temperature profiles in tissue suitable for treating sebaceous follicle disorders. Monte Carlo simulations of light transport and finite difference numerical calculations of temperature distribution identified initial heating and cooling parameters for testing in ex vivo and in vivo models.

Specifically, stochastic Monte Carlo simulations of light transport were performed to calculate the light distribution within a tissue. Given the light distribution and the absorption coefficient, the heat generated by the light was calculated at different depths within the tissue. Numerical finite difference heat transfer calculations taking into account the cooling provided by the cryogen spray were performed to calculate the spatial thermal profiles in tissue at various time points. The temperature profiles are indicative of the tissue damage produced and detailed calculations of thermal damage were done using a kinetic model. Such calculations are a valuable tool in evaluating various heating and cooling schemes to produce desired temperature profiles and can be used as a guide in actual ex vivo or in vivo experiments.

The kinetic thermal damage model relates the temperature-time history of tissue to the thermal damage. The thermal damage measure, Q, is traditionally defined as the logarithm of the ratio of the original concentration of native tissue to the remaining native state tissue and by using a kinetic model, it is given at a time (t) by the formula:

$$\Omega(t) = \ln\{C(0)/C(t)\} = {}_0\int^t \{A \exp(-E_a/RT(\tau))\} d\tau$$

where A is a pre-exponential factor, $E_a$ is the activation energy, R is the Boltzmann constant, and $T(\tau)$ is the thermal history as a function of time (Pearce and Thomsen (1995) "Rate process analysis of thermal damage," in "OPTICAL-THERMAL RESPONSE OF LASER-IRRADIATED TISSUE" Welch and van Gemert, eds., Plenum Press, pp. 561–603). The characteristic behavior of the kinetic damage model is that, below a threshold temperature, the rate of damage accumulation is negligible, and it increases precipitously when this value is exceeded. This behavior is to be expected from the exponential nature of the function. Pearce and Thomsen, supra, define a critical temperature, $T_{crit}$, as the temperature at which the damage accumulation rate, $d\Omega/dt$ is 1.0. Id. This criterion gives $T_{crit}$ as $E_a/R \ln(A)$. A range of values for $T_{crit}$ from 60° C. to 85° C. has been reported for various human tissue (Pearce and Thomsen (1995) supra). For example, Stoll and Weaver report a critical temperature of 60° C. for human skin (Weaver and Stoll (1969) "Mathematical model of skin exposed to thermal radiation" AEROSPACE MED. 40:24).

Monte Carlo and heat transfer calculations were performed using appropriate scattering and absorption properties at each laser wavelength (Table 2). Heat transfer calculations were performed numerically by a finite-difference method taking into account the cooling due to the cryogen (tetrafluoroethane, an EPA approved refrigerant) and heating due to the laser absorption by tissue.

TABLE 2

Optical Properties Used in Monte Carlo Model for Light Distribution

| Property→ Component↓ | Refractive Index, n | Absorption Coefficient, $\mu_a$ | Scattering Coefficient, $\mu_s$ | Anisotropy factor, g |
|---|---|---|---|---|
| Air | 1 | 0 | 0 | 0 |
| Skin | 1.37 | 20 cm$^{-1}$ | 120 cm$^{-1}$ | 0.9 |

TABLE 3

Values of Parameters Used in Heat Transfer Calculations

| Laser Optical Power | Laser Duration | Cryogen Temp. | No. of 100 ms cooling cycles | Spray duration per cycle | Pre-, post-laser spray duration | Cryogen-skin heat transfer coefficient |
|---|---|---|---|---|---|---|
| 10.5 W | 300 ms | −26° C. | 3 | 50 ms | 30, 30 ms | 5000 W/m$^2$K |

Figure 5:
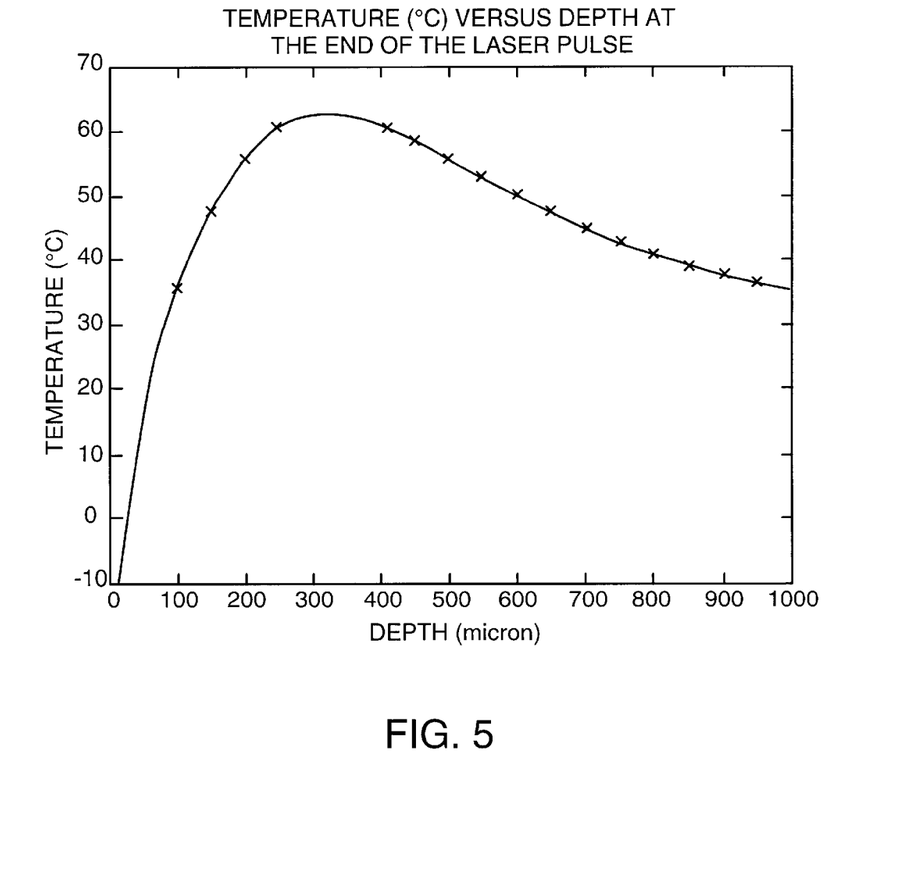
FIG. 5 is a plot showing a profile of temperature (° C.) versus depth through skin (microns) resulting from exemplary heating and cooling phases.

In the calculations, laser energy was delivered for 300 ms at a power of 10.5 W. Simultaneously with the beginning of the laser, the first of the three cryogen cooling cycles were delivered. Each cooling cycle lasted for 100 ms, each comprising 50 ms of spray and 50 ms of no spray. Such a cooling scheme provides almost constant cooling of the top layer of the skin and is expected to lead to epidermal preservation. Spatial temperature profiles were calculated at various times for a typical set of heating and cooling parameters expected to be effective in treatment. FIG. 5 shows the temperature (° C.) plotted versus depth (microns) at the end of the laser pulse. Since tissue temperature in the dermal band centered at about 300 micron exceeds 60° C., a critical temperature reported for skin (Weaver and Stoll (1969) supra), thermal alteration of tissue is expected in this region of skin.

Figure 6:
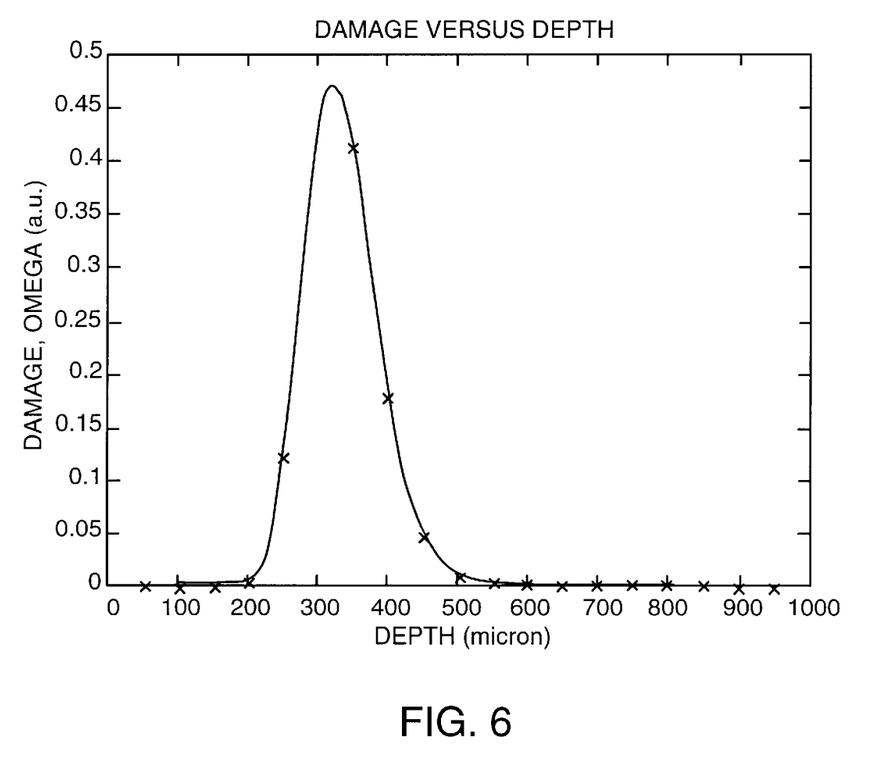
FIG. 6 is a plot showing a profile of tissue damage (Omega a.u.) versus depth through skin (microns) resulting from exemplary heating and cooling phases.

In addition, calculations were performed to determine the extent of tissue damage as a function of depth. Parameters inputted into the kinetic thermal damage model were $E_a = 6.28 \times 10^5$ J/mole and $A = 3.1E98$ s$^{-1}$ to give a $T_{crit}$ value of 60.1° C. The calculated temperature profile through the center of the treatment area as a function of depth is shown in FIG. 5. The peak temperature occurs at a depth of about 300 microns. FIG. 6 depicts the damage predicted by the kinetic thermal damage model as a function of depth. Although the magnitude of the damage depends strongly on the parameters used in the expression for damage, based on these calculations, it is estimated that a thermal damage band occurs between the depths from about 220 microns to about 450 microns. Because sebaceous glands typically are located from about 200 to about 1000 microns from the skin surface, the zone of thermal damage predicted by the foregoing calculations likely would contain sebaceous glands.

Example 2

Ex Vivo Pig Skin Study

To assess if it was possible to preserve skin epidermis while damaging the dermis as well as to assess the zone of dermal damage, experiments were performed ex vivo with freshly excised white pig skin samples.

The temperature of the skin sample was maintained at 30° C. by placing the sample on a warm 1 inch teflon pad and by simultaneous heating from the top with a heat lamp. Several spots on the skin were irradiated using different heating and cooling parameters. A spot size of 4 mm was irradiated using a diode laser system having a wavelength of 1.45 microns and with an optical power of 14 W. A scheme for the timing of the cryogen spray was used that provided almost simultaneous cooling of the skin to preserve the epidermis. The heating and cooling were turned on for a time period ranging from 100 ms to 300 ms. Energy fluences at the skin surface as high as 33 J/cm$^2$ were used. Immediate post-treatment 4-mm punch biopsies were performed and the biopsy samples fixed in 10% buffered formalin solution. The samples were processed and stained with hemotoxylin and eosin (H&E) stain and analyzed under an optical microscope. Thermally denatured collagen appears purple whereas the non-damaged collagen appears pink with this stain under visual examination. The results are summarized in Table 4.

TABLE 4

Values of Parameters used and Observations

| Laser (ms) | Cooling #x (ms + ms) | Energy/pulse (J) | Epidermis condition (biopsy observation) | Depth of the band of thermal damage (estimated by biopsy) |
|---|---|---|---|---|
| 200 | 3x (30 + 70) | 2.82 | epidermis separated | 000→500 μm (500 μm) |
| 200 | 3x (40 + 60) | 2.82 | epidermis spared | left cut: 100→400 μm (300 μm) right cut: 200→300 μm (100 μm) |
| 200 | 3x (50 + 50) | 2.82 | epidermis spared | 150→300 μm (150 μm) |
| 200 | 3x (60 + 40) | 2.82 | epidermis intact | none |
| 200 | 3x (70 + 30) | 2.82 | epidermis intact | none |

In Table 4, the first column provides the total time during which the laser was turned on. The second column provides the cooling parameters. The cooling period was divided into different number of cycles, each lasting 100 ms. Each cooling period having a certain duration when cooling spray was applied and the remainder when no cooling spray was applied. For example, the cooling parameter of 3×(30+70) comprises 300 ms of total cooling with the following timing: (30 ms spray+70 ms no spray)+(30 ms spray+70 ms no spray)+(30 ms spray+70 ms no spray). The last 100 ms cycle is the post-laser spray. The third column provides the total laser energy per pulse. The fourth column provides the epidermal condition as observed by microscopic observation of the biopsy. The fifth column provides the depth of the band of thermal damage as observed in the skin by microscopic observation.

Some notable observations for 200 ms of laser and different cooling parameters are shown in Table 4. With 200 ms of laser at 14 W and 3 cycles of cooling, each lasting 100 ms and comprising of 40 ms of spray and 60 ms of no spray, thermal damage was localized to a zone ranging from about 100 to about 400 microns in depth from the skin surface while at the same time preserving the epidermis.

Example 3

Human Study

Similar treatment parameters as described in the above pig skin study were used to treat sites behind the ear in a human study. Examination of biopsies taken immediately after the treatment showed that sebaceous glands were damaged while skin epidermis was completely spared.

In a separate study, 4 mm spots at periauricular sites (behind the ear) were irradiated, again, with varying combinations of heating and cooling parameters. Heating was provided by a 12 W CW 1.45 micron laser and cooling was provided with a DCD system available from Candela. The heating phase included a single 300 ms exposure to coherent light produced by the 12 W CW 1.45 micron laser. Cooling was accomplished by means of three cooling cycles of 100 ms in duration, with each cooling cycle comprising 20 ms of cryogen spray and 80 ms of no cryogen spray. Two treatments were performed per site.

The results confirmed that it is possible to induce thermal alteration of sebaceous glands extending 200–400 micron in the dermis while preserving the epidermis. Using these parameters, no significant visible epidermal side-effects were detectable. Because this experiment confirms that it is possible to selectively alter sebaceous glands disposed in human tissue, it is contemplated that the parameters employed may also be useful in ameliorating within a preselected region the symptoms, for example, reducing the size and/or density of cysts, papules, pustules, associated with the sebaceous follicle disorder.

Example 4

Rat Study

Rat studies may also be used to further characterize and delineate optimal heating and cooling parameters useful in ameliorating lesions associated with a sebaceous follicle disorder prior to initiation of a systemic human trial.

In particular, experiments can be used to demonstrate the (1) alteration of the sebaceous glands and associated structures, (2) epidermal preservation, and (3) effectiveness of different parameter ranges. The aim of the pilot study is to determine if thermal alteration of the sebaceous glands is possible and to determine approximately the effective range of parameters which at the same time minimize side-effects such as blisters and scars.

A laser beam of 1.45 micron wavelength at 14 W optical power will be used. The parameters shall span the following range: laser, 50 ms–400 ms; cooling cycle, 100 ms; spray, 20–80 ms per cooling cycle. For example, 2 cycles of 20 ms per cooling involves 20 ms spray+80 ms no spray+20 ms spray+80 ms no spray. The number of cooling cycles will match the laser time. For example, 2 cooling cycles will be used for laser times ranging from 200–290 ms. Additional sprays, each lasting 30 ms, will be employed before and after laser treatment. A preferred set of parameters is 250 ms of laser at 14 W, with 30 ms spray/100 ms cooling cycle, and pre-laser and post-laser sprays of 30 ms each.

Histology of biopsies will be used to quantitatively assess the thermal alteration of the sebaceous glands. These results will be used to tune the heating and cooling treatment parameters for the next rat. For example, if the epidermis is not spared, duration of cooling spray will be increased. If the alteration of the sebaceous glands is not large enough, heating times will be increased. It is contemplated that such iterations will give an optimum set of heating and cooling parameters.

Seven white hairless male rats each having reached puberty (ages 7 to 8 weeks) will be used in the initial study. Each rat will be treated and examined one at a time. Data obtained will be used in improving the parameters for further treatment.

Sebutape will be placed on various parts of a first rat for an hour, and the sebum producing areas on the rat skin determined. On the following day, the experiment will be repeated to demonstrate the reproducibility of the sebutape technique for identifying zones of sebum production. Then, the rat will be sacrificed and skin biopsies taken at various sites on the body to map the density of occurrence of sebaceous glands over the back, the belly, and the ears of the rat. The results will be correlated with the results from the sebutape measurements.

The remaining rats will them be treated and alterations to the structure and/or function of the sebaceous glands will be measured. A second rat will be allowed to acclimatize for 3 days. On day zero, six areas for treatment will be delineated on the rat's back with a felt tip pen or tattoo. Each treatment area will be made large enough to provide at least two biopsies. Also, on day zero, a control biopsy will be taken, assuming that there is no large variation in sebaceous glands density over the back as observed with the sebutape and biopsy experiments on the first rat. Also, on day zero, six different marked areas will be treated with six different parameter sets; one set may consist of only cryogen and no laser. Also, on day zero, after two hours, 'immediate' post-operative biopsies of all treatment sites will be taken and each wound sutured. Six biopsies will be obtained. On day 1, i.e., 24-hour post-treatment, the animal will be sacrificed by administration of sodium pentobarbital and six necropsies of the treated areas will be obtained.

Histology analysis will include quantification of alteration to sebaceous glands as well as measurement of fibroblasts, fibrocytes, collagen content and type, epithelial cells, and dermal characteristics. H&E and viability stains will also be used. Histological analyses of immediate biopsies and 24-hour necropsies will be used to assess the alteration of the sebaceous glands. These results will be used to tune the heating and cooling treatment parameters for the next rat. Successful treatment shall be estimated when there is a reduction in size or alteration of the sebaceous glands by at least 25%.

Equivalents

While the invention has been particularly shown and described with reference to specific embodiments, it should be understood by those skilled in the art that various changes in form and detail may be made therein without departing from the spirit and scope of the invention as defined by the appended claims.

Incorporation By Reference

The content of each patent publication and scientific article identified hereinabove is expressly incorporated by reference herein.

What is claimed is:

1. A method of treating a sebaceous follicle disorder in a preselected dermal region of mammalian skin, the preselected dermal region having at least one lesion characteristic of the disorder disposed therein, the method comprising the steps of:
   (a) cooling an area of the skin above the preselected dermal region; and
   (b) applying energy to the preselected dermal region, in the absence of an exogenously provided energy absorbing material, in an amount sufficient to ameliorate the lesion while keeping the temperature of the area of the skin above the preselected dermal region below about 60° C. before, during, or before and during the application of the energy.

2. The method of claim 1, wherein in step (b) the energy is provided by laser light, incoherent light, microwaves, ultrasound or RF current.

3. The method of claim 1 wherein in step (b) the energy is provided by laser light.

4. The method of claim 3, wherein the laser light comprises a wavelength in the range from about 0.6 microns to about 1.8 microns.

5. The method of claim 4, wherein the wavelength is in the range from about 1.2 to about 1.7 microns.

6. The method of claim 5, wherein the wavelength is in the range from about 1.3 to about 1.6 microns.

7. The method of claim 6, wherein the wavelength is about 1.5 microns.

8. The method of claim 7, wherein the fluence is in the range from about 10 to about 150 joules per square centimeter.

9. The method of claim 3, wherein the laser light comprises a fluence in the range from about 5 to about 500 joules per square centimeter.

10. The method of claim 1, wherein the laser light comprises a power density in the range from about 1 to about 10,000 watts per square centimeter.

11. The method of claim 1, wherein step (a) occurs prior to step (b).

12. The method of claim 1 or 11, wherein step (a) occurs contemporaneously with step (b).

13. The method of claim 1, wherein the disorder is acne.

14. The method of claim 13, wherein the acne is acne vulgaris.

15. The method of claim 1 or 13, wherein applying energy in step (b) reduces the size of a lesion disposed within the preselected region.

16. The method of claim 1 or 13, wherein applying energy in step (b) reduces the density of lesions disposed within the preselected region.

17. The method of claim 1 or 13, wherein applying energy in step (b) reduces lesion-associated skin inflammation in the preselected region.

18. A method of treating acne in a preselected dermal region of mammalian skin, the preselected dermal region having at least one acne lesion disposed therein, the method comprising the steps of:
   (a) cooling an area of the skin above the preselected dermal region; and
   (b) exposing the preselected dermal region to a beam of radiation comprising a wavelength in the range from 1.3 microns to 1.6 microns to ameliorate the lesion while keeping the temperature of the area of the skin above the preselected dermal region below about 60° C. before, during, or before and during the exposure to the beam of radiation.

19. The method of claim 18, wherein the wavelength is about 1.5 microns.

20. The method of claim 18, wherein in step (b) the beam of radiation has a fluence in the range from about 5 to about 500 joules per square centimeter.

21. The method of claim 20, wherein the fluence is in the range from about 10 to about 150 joules per square centimeter.

22. The method of claim 18, wherein in step (b) the beam of radiation has a power density in the range from about 1 to about 10,000 watts per square centimeter.

23. The method of claim 22, wherein the power density is in the range from about 5 to about 5,000 watts per square centimeter.

24. The method of claim 18, wherein step (a) occurs prior to step (b).

25. The method of claim 18 or 24, wherein step (a) occurs contemporaneously with step (b).

26. The method of claim 18, comprising the additional step of prior to step (b) providing a radiation absorbing material to the preselected dermal region.

27. The method of claim 18, wherein the disorder is acne vulgaris.

28. The method of claim 18, wherein applying energy in step (b) reduces the size of a lesion disposed with the preselected dermal region.

29. The method of claim 18 or 28, wherein applying energy in step (b) reduces the density of lesions disposed within the preselected region.

30. The method of claim 18 or 28, wherein applying energy in step (b) reduces lesion-associated skin-inflammation in the preselected dermal region.

* * * * *

(12) EX PARTE REEXAMINATION CERTIFICATE (7460th)
United States Patent
Durkin et al.

(10) Number: US 6,743,222 C1
(45) Certificate Issued: Apr. 20, 2010

(54) METHOD OF TREATING DISORDERS ASSOCIATED WITH SEBACEOUS FOLLICLES

(75) Inventors: Anthony J. Durkin, Costa Mesa, CA (US); Dilip Y. Paithankar, Natick, MA (US)

(73) Assignee: Candela Corporation, Wayland, MA (US)

Reexamination Request:
No. 90/010,112, Feb. 22, 2008
No. 90/010,567, Jul. 10, 2009

Reexamination Certificate for:
Patent No.: 6,743,222
Issued: Jun. 1, 2004
Appl. No.: 09/731,496
Filed: Dec. 7, 2000

Related U.S. Application Data
(60) Provisional application No. 60/170,244, filed on Dec. 10, 1999.

(51) Int. Cl.
*A61B 18/18* (2006.01)

(52) U.S. Cl. .................. 606/9; 606/10; 606/13; 606/22; 606/27; 606/3; 607/88; 607/89

(58) Field of Classification Search .................. None
See application file for complete search history.

(56) References Cited

U.S. PATENT DOCUMENTS

| | | | |
|---|---|---|---|
| 3,092,111 A | 6/1963 | Saperstein et al. | |
| 4,930,504 A | 6/1990 | Diamantopoulos et al. | |
| 5,810,801 A | 9/1998 | Anderson et al. | |
| 5,814,040 A | 9/1998 | Nelson et al. | |
| 6,183,773 B1 | 2/2001 | Anderson | |
| 6,235,016 B1 | 5/2001 | Stewart | |
| 6,290,713 B1 | 9/2001 | Russell | |
| 6,402,739 B1 | 6/2002 | Neev | |
| 6,605,080 B1 | 8/2003 | Altshuler et al. | |

OTHER PUBLICATIONS

Burkhart, C.G., et al., "Acne: A Review of Immunologic and Microbiologic Factors", Postgrad. Med. J., 75(884):328–31 (Jun. 1999).
Kjeldstad, et al., "A $31_{P-NMR}$ Study of Propionibacterium acnes, Including Effects Caused By Near–Ultraviolet Irradiation", Biochimica et Biophysica Acta, 927:184–189 (1987).
Finnerud, "Common Skin Diseases of Children," *The Elementary School Journal*, vol. 29, No. 7, pp. 538–546 (1929).
Scott, "Seborrhoeic Skin Eruptions," *British Journal of Dermatology*, vol. 56 Issue 3–4, pp. 80–91 (1946).
Order for Closure, Civil Action No. 1:06–cv–11410–JLT, Dec. 1, 2008 (2 pages).
Letter Regarding the Reexamination of Patent No. 6,743,222 (Control No.: 90/010,112) from Donna M. Meuth, Representative for Requestor, Dec. 15, 2008 (5 pages).
Reilly, "Juvenile Acne," *The American Journal of Nursing* vol. 50, cover page and pages 269–271 (1950).

*Primary Examiner*—Cary E. O'Connor (57) ABSTRACT

Disclosed herein is a method of treating mammalian, for example, human, skin afflicted with a sebaceous follicle disorder, for example, acne. The method involves cooling an exposed surface of a region afflicted with the disorder and applying energy, for example, energy from a coherent or incoherent light source, to the region. The applied energy reduces the size and/or density of lesions associated with the disorder in the treated region, and can reduce or otherwise alleviate lesion-asociated skin inflammation in the treated region. Cooling preserves the surface, for example, epidermis, of the skin. The method, therefore, is effective at treating the disorder while at the same time avoiding or minimizing thermal damage to the exposed surface of the skin.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 26 is cancelled.

Claims 1 and 18 are determined to be patentable as amended.

Claims 2–17, 19–25 and 27–30, dependent on an amended claim, are determined to be patentable.

New claims 31–52 are added and determined to be patentable.

1. A method of treating a sebaceous follicle disorder in a preselected dermal region of mammalian skin, [the preselected dermal region having at least one lesion characteristic of the disorder disposed therein,] the method comprising the steps of:
   (a) cooling an area of the skin above the preselected dermal region; and
   (b) applying energy to the preselected dermal region, in the absence of an exogenously provided energy absorbing material, in an amount sufficient *to cause thermal injury to the preselected dermal region while preserving the sebaceous gland* to ameliorate [the] *at least one* lesion *characteristic of the sebaceous follicle disorder while keeping the temperature of the area of the skin above the preselected dermal region below about 60° C. before, during, or before and during the application of the energy.*

18. A method of treating acne in a preselected dermal region of mammalian skin, [the preselected dermal region having at least one acne lesion disposed therein,] the method comprising the steps of:
    (a) cooling an area of the skin above the preselected dermal region; and
    (b) exposing the preselected dermal region to a beam of radiation comprising a wavelength in the range from 1.3 microns to 1.6 microns *to cause thermal injury to the preselected dermal region while preserving the sebaceous gland* to ameliorate [the] *at least one acne* lesion *while keeping the temperature of the area of the skin above the preselected dermal region below about 60° C. before, during, or before and during the exposure to the beam of radiation.*

31. *The method of claim 1 wherein the thermal injury causes a structural change to the sebaceous follicle.*

32. *The method of claim 1 wherein the thermal injury causes a functional change to the sebaceous follicle.*

33. *The method of claim 32 wherein the functional change reduces sebum production.*

34. *The method of claim 33 wherein the functional change reduces the activity of sebum producing cells.*

35. *The method of claim 33 wherein the functional change destroys sebum producing cells in the sebaceous follicle.*

36. *The method of claim 1 wherein the thermal injury elevates the temperature of the preselected dermal region to cause cell death.*

37. *The method of claim 36 wherein cell death results in the killing of p. acnes.*

38. *The method of claim 32 wherein applying energy in step (b) reduces the size of a lesion disposed within the preselected region.*

39. *The method of claim 32 wherein applying energy in step (b) reduces the density of lesions disposed within the preselected region.*

40. *The method of claim 32 wherein applying energy in step (b) reduces the lesion-associated skin inflammation in the preselected region.*

41. *The method of claim 37 wherein applying energy in step (b) reduces the lesion-associated skin inflammation in the preselected region.*

42. *The method of claim 1 wherein in step (b) the energy is provided by an incoherent beam of radiation.*

43. *The method of claim 42 wherein the beam of radiation comprises a wavelength in the range from about 0.6 microns to about 1.8 microns.*

44. *The method of claim 42 wherein the beam of radiation comprises a wavelength in the range from about 0.8 microns to about 1.2 microns.*

45. *The method of claim 42 wherein applying energy in step (b) elevates the temperature of the preselected dermal region resulting in the killing of p. acnes to reduce lesion-associated skin inflammation in the preselected dermal region.*

46. *A method of treating a disorder of a sebaceous follicle having a sebaceous gland, within a preselected dermal region of mammalian skin, the method comprising the steps of:*
    *(a) cooling an area of the skin above the preselected dermal region; and*
    *(b) applying energy to the preselected dermal region, in the absence of an exogenously provided energy absorbing material, in an amount sufficient (i) to cause thermal injury to the preselected dermal region and (ii) to enable sebum produced by the sebaceous gland to flow out of the sebaceous follicle, to ameliorate at least one lesion characteristic of the disorder while keeping the temperature of the area of the skin above the preselected dermal region below about 60° C. before, during, or before and during the application of the energy.*

47. *The method of claim 46 wherein applying energy in step (b) reduces the size of a lesion disposed within the preselected dermal region.*

48. *The method of claim 46 wherein applying energy in step (b) reduces the density of lesions disposed within the preselected dermal region.*

49. *The method of claim 46 wherein applying energy in step (b) reduces lesion-associated skin inflammation in the preselected dermal region.*

50. *The method of claim 46 wherein applying energy in step (b) causes a functional change to the sebaceous follicle that destroys sebum producing cells.*

51. *The method of claim 46 wherein in step (b) the energy is provided by an incoherent beam of radiation.*

52. *The method of claim 51 wherein applying energy in step (b) elevates the temperature of the preselected dermal region resulting in the killing of p. acnes to reduce lesion-associated skin inflammation in the preselected dermal region.*

* * * * *